US009782455B2

(12) United States Patent
Wellings

(10) Patent No.: US 9,782,455 B2
(45) Date of Patent: Oct. 10, 2017

(54) SOLID PHASE SYNTHESIS OF H(GLY2)GLP-2

(75) Inventor: Don Wellings, Northwich (GB)

(73) Assignee: NPS PHARMACEUTICALS, INC., Bedminster, NJ (US)

( * ) Notice: Subject to any disclaimer, the term of this patent is extended or adjusted under 35 U.S.C. 154(b) by 0 days.

(21) Appl. No.: 13/820,082

(22) PCT Filed: Aug. 30, 2011

(86) PCT No.: PCT/EP2011/064877
§ 371 (c)(1),
(2), (4) Date: Aug. 22, 2017

(87) PCT Pub. No.: WO2012/028602
PCT Pub. Date: Mar. 8, 2012

(65) Prior Publication Data
US 2013/0310314 A1 Nov. 21, 2013

(30) Foreign Application Priority Data

Aug. 30, 2010 (EP) .................................... 10174559

(51) Int. Cl.
A61K 38/26 (2006.01)
C07K 14/605 (2006.01)
A61K 38/00 (2006.01)

(52) U.S. Cl.
CPC ............ A61K 38/26 (2013.01); C07K 14/605 (2013.01); A61K 38/00 (2013.01)

(58) Field of Classification Search
None
See application file for complete search history.

(56) References Cited

FOREIGN PATENT DOCUMENTS

| GB | WO 2006/117565 | * 11/2006 | ........... C07K 14/605 |
|---|---|---|---|
| JP | 2002-502369 | 1/2002 | |
| JP | 2004-532819 | 10/2004 | |
| JP | 2010-509197 | 3/2010 | |
| WO | WO 98/52600 | 11/1998 | |
| WO | WO 02/066511 | 8/2002 | |
| WO | 2007/120614 | 10/2007 | |
| WO | WO 2007/120614 | 10/2007 | |
| WO | WO 2008/056155 | 5/2008 | |
| WO | 2012/028602 | 3/2012 | |

OTHER PUBLICATIONS

Mergler et al., Journal of Peptide Science (2003) 9, 36-46.*
Brandtner et al., John W. Crabb (ed.) (1995) Techniques in Protein Chemistry VI. Orlando FL: Academic Press, 547-554.*
Novabiochem Catalog, 2012/2013 (1994-2012) Darmstadt, Germany: Merck KgaA, 187.*
Mergler et al., Journal of Peptide Science (2003) 9, 518-526.*
Isidro-Llobet, Chem. Rev. (2009) 109, 2455-2504.*
Cebrian, et al., "Synthesis of peptide sequences related to thrombospondin: Factors affecting aspartimide by-product formation", Journal of Peptide Research, vol. 62:6, Dec. 2003, p. 238-244.
Hendrix, et al., "Synthesis of a protected peptide corresponding to residues 1-25 of the beta-amyloid protein of alzheimer's disease", Journal of Organic Chemistry, ACS, vol. 57:12, Jan. 1992, p. 3421-3426.
Jaroslaw, et al., "Problem of aspartimide formulation in Fmoc-based solid phase peptide synthesis using Dmab group to protectside chain of aspartic acid", Journal of Peptide Science, vol. 14:3, Mar. 2008, p. 335-341.
Kent, "Chemical synthesis of peptides and proteins", Annual Review of Biochemistry, vol. 57, Jan. 1988, p. 957-989.
International Search Report Issued in PCT/EP2011/064877 on Dec. 28, 2011.
Written Opinion Issued in PCT/EP2011/064877 on Feb. 28, 2013.
Extended European Search Report mailed Jan. 25, 2016 as received in EP Application No. 15183374.6.

* cited by examiner

Primary Examiner — Marcela M Cordero Garcia
Assistant Examiner — Catherine Mader

(57) ABSTRACT

The present invention relates to a method of preparing a peptide comprising the amino acid sequence His-Gly-Asp-Gly-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp (SEQ ID NO:1). In particular, the method comprises the steps of providing a first peptide fragment having a first protection group, which peptide fragment is conjugated to a support; providing a second peptide fragment having a second protection group; removing the first protection group from the first peptide fragment; and coupling the second peptide fragment to the N-terminally deprotected, support-conjugated first peptide fragment. The present invention further relates to a method of preparing a pharmaceutical composition containing said peptide.

16 Claims, 3 Drawing Sheets

```
                        SEQUENCE LISTING

<160> NUMBER OF SEQ ID NOS: 3

<210> SEQ ID NO 1
<211> LENGTH: 33
<212> TYPE: PRT
<213> ORGANISM: Artificial Sequence
<220> FEATURE:
<223> OTHER INFORMATION: This sequence represents the synthetic
      sequence, Teduglutide, a synthetically derived Glucagon-Like
      Peptide-2 analog.  The sequence comprises human Glucagon-Like
      Peptide-2 with an Ala2 to Gly2 substitution.

<400> SEQUENCE: 1

His Gly Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 2
<211> LENGTH: 29
<212> TYPE: PRT
<213> ORGANISM: Homo sapiens

<400> SEQUENCE: 2

Ser Phe Ser Asp Glu Met Asn Thr Ile Leu Asp Asn Leu Ala Ala Arg
1               5                   10                  15

Asp Phe Ile Asn Trp Leu Ile Gln Thr Lys Ile Thr Asp
            20                  25

<210> SEQ ID NO 3
<211> LENGTH: 4
<212> TYPE: PRT
<213> ORGANISM: Artificial Sequence
<220> FEATURE:
<223> OTHER INFORMATION: The synthetic sequence represents amino acids
      1-4 of Teduglutide, presented as SEQ ID NO: 1

<400> SEQUENCE: 3

His Gly Asp Gly
1
```

SOLID PHASE SYNTHESIS OF H(GLY2)GLP-2

SUBJECT OF THE INVENTION

Figure 1:
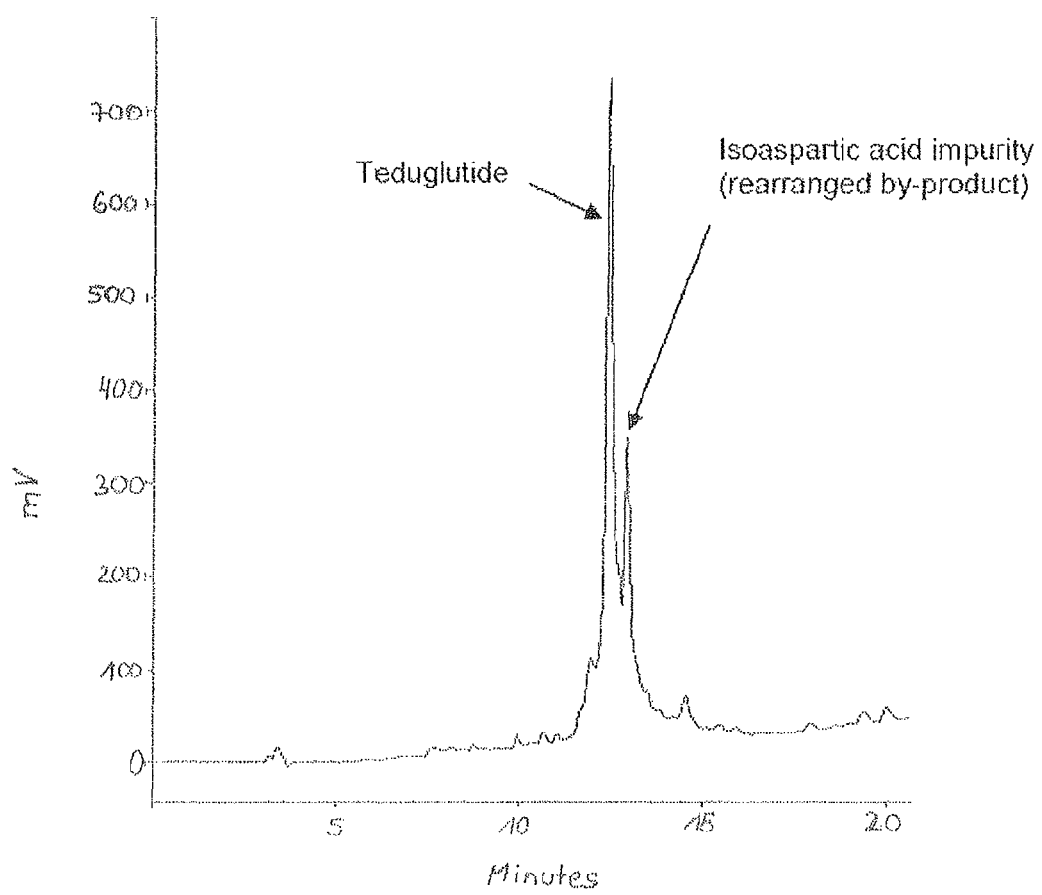

The present invention relates to a method of preparing a peptide comprising the amino acid sequence His-Gly-Asp-Gly-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp (SEQ ID NO:1). In particular, the method comprises the steps of providing a first peptide fragment having a first protection group, which peptide fragment is conjugated to a support; providing a second peptide fragment having a second protection group; removing the first protection group from the first peptide fragment; and coupling the second peptide fragment to the N-terminally deprotected, support-conjugated first peptide fragment. The present invention further relates to a method of preparing a pharmaceutical composition containing said peptide.

BACKGROUND OF THE INVENTION

Glucagon-like peptide-2 (GLP-2) is a 33 amino acid peptide having therapeutic applications in the treatment of diseases of the gastrointestinal tract. This naturally occurring hormone has been shown to regulate the growth, proliferation and maintenance of cells lining the gastrointestinal tract. In particular, it has been determined that GLP-2 and analogs thereof act as trophic agents to enhance and maintain the functioning of the gastrointestinal tract and to promote growth of intestinal tissue (see, e.g., European patent application EP 1 246 639 A2).

Teduglutide, hereinafter also referred to as "h[Gly2]GLP-2", is a single-chain and non-glycosylated 33-amino acid peptide having the following sequence:

(SEQ ID NO: 1)
His$^1$-Gly$^2$-Asp$^3$-Gly$^4$-Ser$^5$-Phe$^6$-Ser$^7$-Asp$^8$-Glu$^9$-Met$^{10}$-

Asn$^{11}$-Thr$^{12}$-Ile$^{13}$-Leu$^{14}$-Asp$^{15}$-Asn$^{16}$-Leu$^{17}$-Ala$^{18}$-

Ala$^{19}$-Arg$^{20}$-Asp$^{21}$-Phe$^{22}$-Ile$^{23}$-Asn$^{24}$-Trp$^{25}$-Leu$^{26}$-

Ile$^{27}$-Gln$^{28}$-Thr$^{29}$-Lys$^{30}$-Ile$^{31}$-Thr$^{32}$-Asp$^{33}$

This analog of GLP-2 differs from native GLP-2 by a change in one amino acid, i.e. alanine is replaced by glycine in position 2. This change has been determined to result in a peptide with a longer half-life. In particular, animal studies indicate that administration of this peptide produces a significant increase in both the mass and absorptive surface area of the epithelium lining the intestine, and moreover has a pronounced effect on reducing gut permeability.

As many other therapeutic peptides, this GLP-2 analog can be manufactured recombinantly by expression in E. coli. However, in order to increase the production yield and to eliminate the need for some animal-derived raw materials in production, there was a need to provide alternative methods of preparing teduglutide.

In the prior art, several solutions have been sought for chemically synthesizing peptides in general.

Solid-phase peptide synthesis (SPPS) is a method introduced by Merrifield in 1963 (J. Amer. Chem. Soc. 1963, 85: 2149-2154). Numerous peptides have been synthesized with this technique since then. A review of the chemical synthesis of peptides and proteins is provided by S. B. H. Kent (Annu. Rev. Biochem. 1988, 57: 957-989).

In general, one strategy for the synthesis of peptide chains by solid-phase synthesis is the stepwise solid-phase synthesis. In stepwise SPPS, the C-terminal amino acid in the form of an N-[alpha]-protected, if necessary side-chain protected reactive derivative is covalently coupled either directly or by means of a suitable linker to a solid support, e.g. a polymeric resin, which is swollen in an organic solvent. The N-[alpha]-protection group is removed, and the subsequent protected amino acids are added in a stepwise fashion. When the desired peptide chain length has been obtained, the side-chain protection groups are removed, and the peptide is cleaved from the support. Over the years, two major coupling strategies have been developed based on the use of different N-[alpha]-protection groups and matching side-chain protection groups. Merrifield used t-butyloxycarbonyl (Boc) as the N-[alpha] protection group, while 9-fluorenyl-methyloxy-carbonyl (Fmoc) was introduced by Carpino and Han (J. Org. Chem. 1972, 37: 3404-3409).

A general synthesis method for the preparation of GLP-2 molecules including teduglutide is described, e.g., in international patent applications WO 2006/117565 and WO 2008/056155. According to these applications, peptides were synthesized batchwise in a polyethylene vessel equipped with a polypropylene filter for filtration using 9-fluorenylmethyloxycarbonyl (Fmoc) as N-[alpha]-amino protection group and suitable common protection groups for side-chain functionalities. The amino acids were coupled as in situ generated N-hydroxybenzotriazole (HOBt) or 1-hydroxy-7-aza-benzotriazole (HOAt) esters made from appropriate N-[alpha]-protected amino acids and HOBt or HOAt by means of diisopropylcarbodiimide (DIC) in DMF. These substances can react with O-acylurea formed by the reaction of DIC and the carboxylic acid group of the amino acid to form an active ester. Deprotection of the Fmoc group was performed by treatment with piperidine in DMF. Subsequently, the peptides were cleaved from the resins by treatment with 95% trifluoroacetic acid (TFA). The crude freeze-dried product was analyzed by high-performance liquid chromatography (HPLC) and identified by mass spectrometry (MS).

According to the prior art, GLP-2 molecules are being considered as candidates for standard chemical synthesis by the Fmoc-solid phase approach. It appeared to be a common understanding that GLP-2 molecules are probably best assembled in a linear fashion by solid phase chemistry due to the relative ease of assembly and the ultimate manufacturing scale. However, numerous side reactions can occur during solid phase synthesis, some of which are specific to the chemistries employed using Fmoc methodology.

In particular, it has been found that one particular problem in the synthesis of teduglutide by Fmoc-solid phase chemistry involves rearrangement of the -Asp-Gly-bond at position 3-4 in the molecule resulting in the formation of the [beta]-Asp analogue (so-called "aspartimide by-product formation"). The [beta]-isomerization of -Asp-Gly- bonds involves the carboxy side-chain group from the aspartic acid forming a peptide bond with the [alpha]-amino group of the adjacent glycine via a succinimide intermediate. The main cause of this reaction is the treatment of the teduglutide-solid phase with piperidine, or other bases during the Fmoc removal stage. This reaction resulting in the undesired by-product is about 10% per N-terminal deprotection cycle but can be significantly higher.

In particular, when teduglutide is assembled at a laboratory scale the piperidine treatment to remove the N-terminal Fmoc protection group usually takes a maximum of ~10 minutes. However, at a large scale addition, filtration and removal of piperidine from the peptide-polymer takes much longer. The slower addition and mixing of reagents at process scale results in an extended exposure of the peptide polymer to piperidine much longer which even may exaggerate the problem of aspartimide by-product formation.

Accordingly, there is a need for alternative synthesis methods for preparing teduglutide, wherein aspartimide by-product formation can be reduced or even avoided. In particular embodiments, such a route of synthesizing teduglutide should also be easy to accomplish and inexpensive. Furthermore, such route of synthesizing teduglutide should be suited for industrial scale.

Administration of therapeutic peptides such as teduglutide further requires compositions that remain stable during storage. Because of their size and the resulting difficulty in crossing biological membranes and because of their susceptibility to digestion, peptides are frequently administered parenterally. However, peptides can be particularly difficult to formulate because of their tendency to degrade over time and/or undergo aggregation and precipitation. Degradation, aggregation, and precipitation are all indicative of an unstable composition which may not be commercially viable. Composition variables which affect the degradation of peptides during storage include pH, the quantity of salts present, and the type and quantity of excipients.

Hence, there is also a need in the art for commercially suitable compositions of teduglutide which can be prepared using a commercially acceptable process.

OBJECT AND SUMMARY OF THE INVENTION

It is an object of the present invention to provide a method of preparing teduglutide, wherein aspartimide formation can be reduced or even avoided. Accordingly, it is a further object of the present invention to provide a method of preparing teduglutide, which method is easy to accomplish and inexpensive. Furthermore, such method of preparing teduglutide should be suited for industrial scale. It is a further object of the present invention to provide a commercially acceptable method of preparing compositions of teduglutide.

According to an embodiment of the present invention, a method of preparing teduglutide is provided which breaks the assembly into two fragments.

It has been found that the method according to the present invention may offer a series of advantages compared to the known synthesis method. In particular, it has been found that the level of rearrangement at the Asp-Gly positions 3-4 can be reduced by preparing the peptide via a fragment based assembly. This means that the peptide can be assembled up to the 5 position by solid phase assembly. The tetrapeptide corresponding to positions 1-4 of teduglutide (His-Gly-Asp-Gly) can be assembled separately, and then optionally be purified to remove the [beta]-Asp analogue before coupling to the 5-33 fragment on the solid phase. Accordingly, the peptide is not subjected to e.g. piperidine following coupling of this tetrapeptide fragment. Surprisingly, the method according to the present invention not only increases the purity of the peptide, but also the overall yield.

These objectives as well as others which will become apparent from the ensuing description are attained by the subject matter of the independent claims. Some of the embodiments of the present invention are defined by the subject matter of the dependent claims.

In one embodiment, the present invention relates to a method of preparing a peptide comprising the amino acid sequence His-Gly-Asp-Gly-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp (SEQ ID NO:1), the method comprising the steps of:

(a) providing a first peptide fragment comprising the amino acid sequence X-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp (SEQ ID NO:2), wherein X is a first protection group and the C-terminal residue of the first peptide fragment is conjugated to a support;

(b) providing a second peptide fragment comprising the amino acid sequence Y-His-Gly-Asp-Gly (SEQ ID NO:3), wherein Y is a second protection group;

(c) removing the first protection group from the first peptide fragment; and (d) coupling the second peptide fragment to the N-terminally deprotected, support-conjugated first peptide fragment.

In one embodiment, the first peptide fragment and/or the second peptide fragment are prepared by solid phase peptide synthesis. For example, the first peptide fragment and/or the second peptide fragment are provided by conjugating the C-terminal amino acid residue to a support and sequentially adding appropriately protected amino acids to the N-terminus of the C-terminal, support-conjugated residue(s).

In particular, amino acids to be sequentially added to the N-terminus of the C-terminal, support-conjugated residue(s) of the first peptide fragment and/or the second peptide fragment can each be protected by a protection group selected from the group consisting of Boc and Fmoc.

In another embodiment of the present invention, the first protection group is Fmoc.

In another embodiment of the present invention, the second protection group is an acid-labile protection group, optionally selected from the group consisting of Boc and benzyloxycarbonyl (Z).

Typically, the histidine residue of the second peptide fragment can be protected at the side chain with a protection group which is e.g. selected from the group consisting of trityl, Boc, Bom and Bum.

Also, the aspartic acid residue of the second peptide fragment can be protected at the side chain, e.g. with a tert-butyl ester protection group.

In another embodiment, prior to coupling the second peptide fragment to the N-terminally deprotected, support-conjugated first peptide fragment the second peptide fragment is cleaved from the support.

In some embodiments, prior to coupling the second peptide fragment to the N-terminally deprotected, support-conjugated first peptide fragment the cleaved second peptide fragment is purified, optionally by chromatography and/or crystallization.

According to one embodiment, the Fmoc protection group can be removed from the first peptide fragment by adding a secondary amine selected from the group consisting of piperidine, piperazine, morpholine and dicyclohexylamine.

According to a further embodiment, the inventive method further comprises cleaving the first peptide fragment coupled to the second peptide fragment from the support.

In another embodiment, the method according to the present invention further comprises purifying the cleaved first peptide fragment coupled to the second peptide fragment, optionally by chromatography.

In a specific embodiment, the present invention relates to a method of preparing a peptide comprising the amino acid sequence His-Gly-Asp-Gly-Ser-Phe-Ser-Asp-Glu-Met-Asn-Thr-Ile-Leu-Asp-Asn-Leu-Ala-Ala-Arg-Asp-Phe-Ile-Asn- Trp-Leu-Ile-Gln-Thr-Lys-Ile-Thr-Asp (SEQ ID NO:1), the method comprising the steps of:

(a) providing a first peptide fragment comprising the amino acid sequence X-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp (SEQ ID NO:2) by peptide synthesis, wherein X is a Fmoc protection group and the C-terminal residue of the first peptide fragment is conjugated to a support;

(b) providing a second peptide fragment comprising the amino acid sequence Y-His-Gly-Asp-Gly (SEQ ID NO:3) by peptide synthesis, wherein Y is an acid-labile protection group, optionally selected from the group consisting of Boc and benzyloxycarbonyl, and the C-terminal residue of the second peptide fragment is conjugated to a support;

(c) cleaving the second peptide fragment from the support;

(d) purifying the cleaved second peptide fragment, optionally by reversed-phase high-pressure liquid chromatography;

(e) removing the Fmoc protection group from the first peptide fragment, optionally by adding a secondary amine selected from the group consisting of piperidine, piperazine, morpholine and dicyclohexylamine;

(f) coupling the second peptide fragment to the support-conjugated first peptide fragment by adding the purified second peptide fragment to the N-terminally deprotected, support-conjugated first peptide fragment;

(g) cleaving the support-conjugated first peptide fragment coupled to the second peptide fragment from the support; and (h) purifying the cleaved first peptide fragment coupled to the second peptide fragment, optionally by reversed-phase high-pressure liquid chromatography.

According to one embodiment, the support is a functionalized polymer, optionally selected from the group consisting of polystyrene, polydimethylacrylamide and polyethyleneglycol.

Usually, the C-terminal amino acid of the first peptide fragment and/or the second peptide fragment is attached to the functionalized polymer by means of a linker, optionally 4-hydroxymethylphenoxyacetic acid (HMPA).

In some embodiments, the first peptide fragment and/or the second peptide fragment are cleaved from the support by means of an acid, optionally selected from the group consisting of trifluoroacetic acid (TFA), trifluoromethanesulfonic acid (TFMSA), hydrogen bromide (HBr), hydrogen chloride (HCl) and hydrogen fluoride (HF), or by means of a base, optionally a hydroxide.

In another aspect, the present invention relates to a method of preparing a pharmaceutical composition containing a peptide comprising the amino acid sequence His-Gly-Asp-Gly-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp (SEQ ID NO:1), the method comprising the steps of:

(a) preparing the peptide according to the method of the present invention as described above; and (b) preparing a pharmaceutical composition containing the peptide prepared in step (a).

In one embodiment, the pharmaceutical composition further comprises a buffer, optionally a phosphate buffer in an amount sufficient to adjust the pH of the composition to a physiologically tolerable level, e.g. at a pH between from about 6 to about 9 or between from about 6.5 to about 8 or between from about 7 to about 7.5.

In another embodiment, the pharmaceutical composition further comprises L-histidine.

Further, the pharmaceutical composition may comprise a bulking agent which is optionally selected from the group consisting of mannitol and sucrose.

According to a specific embodiment, the pharmaceutical composition is provided as an injectable dosage form.

In a further embodiment, the present invention relates to a peptide comprising the amino acid sequence His-Gly-Asp-Gly-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp (SEQ ID NO:1), the peptide being obtainable by the method of the present invention as described above.

FIGURE LEGENDS

FIG. 1 depicts an HPLC of crude teduglutide molecule assembled using the standard Fmoc solid phase procedure (linear assembly). Two major peaks were observed, namely the crude teduglutide peptide (peak 1) and the [beta]-Asp by-product (peak 2). This HPLC shows that the purity of the crude peptide assembled was 52% by HPLC and contained 24% of the [beta]-Asp analogue.

Figure 2:
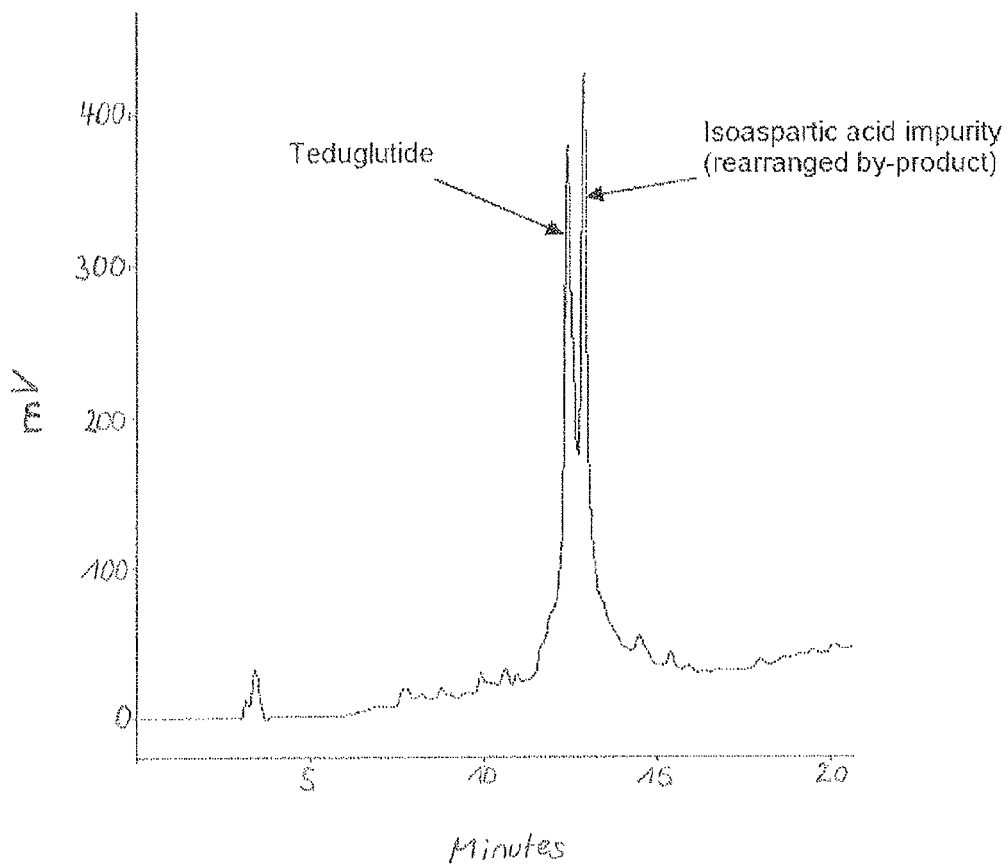

FIG. 2 depicts an HPLC of crude teduglutide molecule assembled using the standard Fmoc-solid phase procedure with extended piperidine treatment for the last 4 amino acids. Two major peaks were observed, namely the crude teduglutide peptide (peak 1) and the [beta]-Asp by-product (peak 2). This HPLC shows that the purity of the crude peptide assembled was only 39% by HPLC and contained 45% of the [beta]-Asp analogue.

Figure 3:
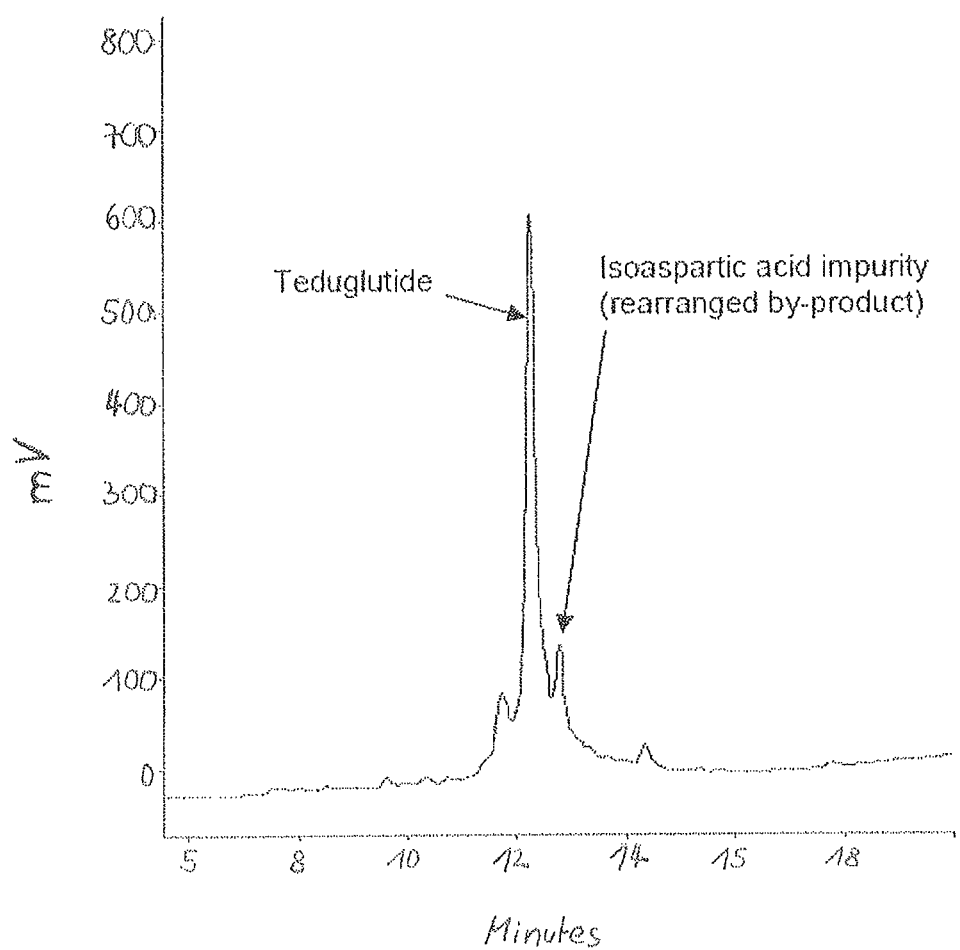

FIG. 3 depicts an HPLC of crude teduglutide molecule assembled using the method according to the present invention (fragment-based assembly). A major peak and a smaller peak were observed, namely the crude teduglutide peptide (peak 1) and the [beta]-Asp by-product (peak 2). This HPLC shows that the purity of the crude peptide assembled was 59% by HPLC and contained only 17% of the [beta]-Asp analogue.

DETAILED DESCRIPTION OF THE INVENTION

The present invention is based on the finding that potential aspartimide by-product formation during the synthesis of teduglutide can be reduced or even avoided by preparing the peptide via a fragment based assembly. The method according to the present invention is capable of providing teduglutide in high yield and/or a high purity. Furthermore, the method according to the present invention can be used to prepare teduglutide at industrial process scale with a high yield and/or a high purity. It has further been found that a crude purity of at least 80% can be achieved by preparing teduglutide according to the method according to the present invention.

Purity and yield are important aspects of any route of peptide synthesis. Purity is represented by the degree of presence of pharmacologically active related impurities (such as the aspartimide by-product). In peptide synthesis repeated purifications at each step lead to a lower yield of the final peptide. The present invention provides a method that achieves a higher purity together with enhanced yield of the target peptide teduglutide through solid phase methodology when compared with known solid phase synthetic methods.

The methods of the present invention will now be described with respect to particular embodiments and with reference to certain drawings but the invention is not limited thereto.

Where the term "comprising" is used in the present description and claims, it does not exclude other elements or steps. For the purposes of the present invention, the term "consisting of" is considered to be an optional embodiment of the term "comprising of". If hereinafter a group is defined to comprise at least a certain number of embodiments, this is also to be understood to disclose a group which optionally consists only of these embodiments.

Where an indefinite or definite article is used when referring to a singular noun e.g. "a" or "an", "the", this includes a plural of that noun unless specifically stated.

The term "about" in the context of the present invention denotes an interval of accuracy that the person skilled in the art will understand to still ensure the technical effect of the feature in question. The term typically indicates deviation from the indicated numerical value of ±10%, and in some embodiments ±5%.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Further definitions of term will be given in the following in the context of which the terms are used.

In one embodiment, the present invention relates to a method of preparing a peptide comprising the amino acid sequence His-Gly-Asp-Gly-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp (SEQ ID NO:1), the method comprising:

(a) providing a first peptide fragment comprising the amino acid sequence X-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp (SEQ ID NO:2), wherein X is a first protection group and the C-terminal residue of the first peptide fragment is conjugated to a support;
(b) providing a second peptide fragment comprising the amino acid sequence Y-His-Gly-Asp-Gly (SEQ ID NO:3), wherein Y is a second protection group;
(c) removing the first protection group from the first peptide fragment; and
(d) coupling the second peptide fragment to the N-terminally deprotected, support-conjugated first peptide fragment.

Hence, the present invention is directed to a method of preparing teduglutide which is a single-chain and non-glycosylated 33-amino acid peptide having the following sequence:

(SEQ ID NO: 1)
$His^1$-$Gly^2$-$Asp^3$-$Gly^4$-$Ser^5$-$Phe^6$-$Ser^7$-$Asp^8$-$Glu^9$-$Met^{10}$-
$Asn^{11}$-$Thr^{12}$-$Ile^{13}$-$Leu^{14}$-$Asp^{15}$-$Asn^{16}$-$Leu^{17}$-$Ala^{18}$-
$Ala^{19}$-$Arg^{20}$-$Asp^{21}$-$Phe^{22}$-$Ile^{23}$-$Asn^{24}$-$Trp^{25}$-$Leu^{26}$-
$Ile^{27}$-$Gln^{28}$-$Thr^{29}$-$Lys^{30}$-$Ile^{31}$-$Thr^{32}$-$Asp^{33}$

This analog of GLP-2 (glucagon-like peptide 2) differs from native GLP-2 by a change in one amino acid, i.e. alanine is replaced by glycine in position 2.

The terms "polypeptide", "peptide", "oligopeptide" and "protein" are used interchangeably herein to refer to a polymer or oligomer of consecutive amino acid residues. The amino acids in such a polymer are joined together by the peptide bonds between the carboxyl and amino groups of adjacent amino acid residues. As used herein, the term "amino acid" refers not only to amino acid molecules or amino acid residues per se, but also to a list of abbreviations, letters, characters or words representing amino acid residues, e.g. amino acid residues being part of a peptide. Amino acids may be referred to herein by either their commonly known three letter symbols or by the one-letter symbols recommended by the IUPAC-IUB Biochemical Nomenclature Commission.

Unless noted otherwise, the N-terminus of the peptide (e.g. at position 1) may be —H or a peptide bond (e.g., it is linked to an N-terminal blocking/protection group or to another amino acid or peptide fragment). Unless noted otherwise, the C-terminus of the peptide (e.g. at position 33) may be —OH or a peptide bond (e.g., it is linked to a C-terminal blocking/protection group or to another amino acid or peptide fragment).

Unless noted otherwise, all amino acid position numbers are the position numbers according to the base sequence of teduglutide as represented by SEQ ID NO:1.

In the context of the present invention, the term "peptide fragment" refers to a specific fragment of teduglutide, in particular a first peptide fragment comprising the amino acid sequence X-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp (SEQ ID NO:2), wherein X is a first protection group, and a second peptide fragment comprising the amino acid sequence Y-His-Gly-Asp-Gly (SEQ ID NO:3), wherein Y is a second protection group.

In one embodiment of the present invention, teduglutide is synthesized by coupling the carboxyl group or C-terminus of one amino acid or peptide fragment to the amino group or N-terminus of another amino acid or peptide fragment. Chemical peptide synthesis usually starts at the C-terminal end of the peptide and ends at the N-terminus. This is the opposite direction to the direction of protein biosynthesis, which starts at the N-terminal end. Due to amino acid excesses typically used to ensure complete coupling during each synthesis step, polymerization of amino acids is common in reactions where each amino acid is not protected. In order to prevent this polymerization, protection groups are typically used in the method according to the present invention.

Suitable protective groups are well-known to a person skilled in the art (e.g., see "Fmoc-Solid Phase Peptide Synthesis-A practical approach", W. C. Chan, P. D. White, Oxford University Press Inc. New York, 2000).

Removing the protection groups from the peptide fragments can e.g. be accomplished by adding a suitable deprotection reagent which depends on the protection group being used. Typical standard protection groups for [alpha]-amino functions of the coupled amino acids are Boc, which can be removed by treatment with a strong acid, or Fmoc, which can be removed with a base. The abbreviations "Fmoc" and "Boc" as used herein mean 9H-fluoren-9-ylmethoxycarbonyl and t-butyloxycarbonyl, respectively.

The t-Boc ("tert-butyloxycarbonyl" or more simply "Boc") group is commonly used for protecting the terminal amine of the peptide, typically requiring the use of more acid stable groups for side chain protection in orthogonal strategies. Boc groups can be added to amino acids with Boc anhydride and a suitable base.

Fmoc (9H-fluoren-9-ylmethoxycarbonyl) is currently a widely used protective group. Fmoc is cleaved under very mild basic conditions (e.g. piperidine). This allows mild acid labile protection groups that are stable under basic conditions, such as Boc and t-butyl groups, to be used on the side-chains of amino acid residues of the target peptide.

According to the method of the present invention, the first peptide fragment comprises a first protection group and the second peptide fragment comprises a second protection group. In some embodiments, the first protection group is different from the second protection group. Alternatively, the first and second protection groups can be identical.

Furthermore, also the side chain functionality in the peptide pre-sequence is typically protected during the coupling steps. More than half of the amino acids commonly encountered in peptides have side chains that contain reactive groups. In peptide synthesis, in particular in solid phase synthesis, it is usual for all these potentially reactive groups to be masked because of the rather harsh conditions employed and the need to achieve the highest level of efficiency in all chemical reactions. For routine synthesis, protection groups that are removed with trifluoroacetic acid (TFA) are usually employed as this allows the peptide to be globally deprotected at the same time as it is cleaved or released from the support. Furthermore, a wide range of groups is also available which can be selectively removed during synthesis (e.g., on the solid phase), thus enabling the selective modification of side chains of individual residues within the peptide chain.

For instance, the Boc group can be used for amino functions (e.g., Lys and His), tert-butyl esters can be used for acidic groups (e.g., Asp and Glu) and tert-butyl ethers can be used for hydroxyl groups (e.g., Tyr, Thr and Ser). Further suitable protection groups for side chain protection are readily available and well-known to a person skilled in the art (e.g., see Table 4 on pages 20-25 in "Fmoc-Solid Phase Peptide Synthesis-A practical approach", W. C. Chan, P. D. White, Oxford University Press Inc. New York, 2000; being incorporated herein by reference).

In one embodiment, the second peptide fragment is coupled to the N-terminally deprotected, support-conjugated first peptide fragment. Most methods of amide bond formation involve chemical activation of the carboxy component. Those commonly employed in organic synthesis are generally regarded as too harsh to be used in peptide synthesis, leading to the formation of over-activated intermediates, which are unselective in their reactions and consequently prone to side reactions. Peptide chemists have therefore sought milder activation methods, mostly based on the formation of active esters, pre-formed or generated in situ.

The rate of the condensation of protected fragments with the resin-bound N-fragment usually increases with the concentration of the fragment. Typically, fragment solutions of the highest possible concentration are applied. Suitable coupling reagents for fragment condensation are readily available and well-known to a person skilled in the art (e.g., see pages 221-223 in "Fmoc-Solid Phase Peptide Synthesis-A practical approach", W. C. Chan, P. D. White, Oxford University Press Inc. New York, 2000; being incorporated herein by reference). DMSO can be used as a solvent. Further, DCC/HOBt (dicyclohexylcarbodiimide/1-hydroxybenzotriazole) or DIC/HOBt (diisopropylcarbodiimide/1-hydroxy-benzotriazole) can be used as condensing agents.

In some embodiments, the first peptide fragment and/or the second peptide fragment are prepared by solid phase peptide synthesis. For instance, the first peptide fragment and/or the second peptide fragment can be provided by conjugating the C-terminal amino acid residue to a support and sequentially adding appropriately protected amino acids to the N-terminus of the C-terminal, support-conjugated residue(s).

Solid phase peptide synthesis (hereinafter referred to as "SPPS") was introduced with the intent to overcome many of the intermediate purification problems associated with solution peptide synthesis. During solid phase synthesis, amino acids are assembled (i.e., coupled) into a peptide of any desired sequence while one end of the chain (e.g. the C-terminus) is anchored to an insoluble support. Once the desired sequence has been linked together on the support, the peptide is then deblocked (i.e., cleaved) from the support. SPPS has the general advantage that it lends itself to fully automated or semi-automated chain assembly chemistry.

The principles of solid phase synthesis are well-known to a person skilled in the art (e.g., see FIG. 1 on page 10 and pages 9-13 in "Fmoc-Solid Phase Peptide Synthesis-A practical approach", W. C. Chan, P. D. White, Oxford University Press Inc. New York, 2000; being incorporated herein by reference). In particular, the C-terminal amino acid residue of the target peptide can be attached to an insoluble support via its carboxyl group. Any functional groups in amino acid side chains could be masked with permanent protection groups that are not affected by the reaction conditions employed during peptide assembly. The temporary protection group masking the [alpha]-amino group during the initial resin loading is removed. An excess of the second amino acid is usually introduced, with the carboxy group of this amino acid being activated for amide bond formation through generation of an activated ester or by reaction with a coupling agent. Suitable coupling agents are readily available and well-known to a person skilled in the art (e.g., see Table 5 on page 28 and pages 52-60 in "Fmoc-Solid Phase Peptide Synthesis-A practical approach", W. C. Chan, P. D. White, Oxford University Press Inc. New York, 2000; being incorporated herein by reference).

After coupling, excess reagents can be removed by washing and the protection group can be removed from the N-terminus of the dipeptide, prior to addition of the third amino acid residue. This process is repeated until the desired peptide sequence is assembled. In a final step, the peptide is released from the support and the side chain protection groups removed. Usually, side chain protection groups and support linkage are chosen such that protection groups are removed and the assembled peptide released under the same conditions.

In designing a synthesis of a peptide by the solid phase method using either of the above mentioned [alpha]-amino protection schemes or any other protection scheme known in the art, it is usually desirable that any reactive "side groups" of the constituent amino acids are protected from unwanted chemical reactions throughout the chain assembly. It can also be desirable that the chemical groups chosen to protect the various side groups are resistant to removal by the reagents used to remove the [alpha]-amino protection groups. Further, the linkage of the growing peptide chain to the support should be stable to the reagents used to remove either type of [alpha]-amino protection group during chain assembly.

In one embodiment, amino acids to be sequentially added to the N-terminus of the C-terminal, support-conjugated residue(s) of the first peptide fragment and/or the second peptide fragment are each protected by a protection group selected from the group consisting of Boc and Fmoc.

In the case of the Fmoc [alpha]-amino protection scheme, the side group protection functions are usually selected to be resistant to the basic reagents used to remove Fmoc. In practice, these side chain protection groups may generally be removed by mildly acidic reagents after the peptide chain has been assembled. When using the Boc [alpha]-amino protection scheme, the side chain protection groups are typically selected to be resistant to removal by the mild acid reagent used to deprotect the Boc group at every cycle. In practice, these side chain protection groups for the Boc [alpha]-amino protection scheme can usually be removed by anhydrous HF after the peptide chain has been assembled. Therefore, in some embodiments, the side chain protection groups commonly used with the Fmoc [alpha]-amino protection are not stable under the conditions used for Boc [alpha]-amino deprotection and the two types of [alpha]-amino protection schemes are not mixed in the assembly of a peptide chain by solid phase peptide synthesis.

The principles of Merrifield SPPS (using Boc) and Fmoc/tBu SPPS (using Fmoc) are well-known to a person skilled in the art (e.g., see pages 11-13 in "Fmoc-Solid Phase Peptide Synthesis-A practical approach", W. C. Chan, P. D. White, Oxford University Press Inc. New York, 2000; being incorporated herein by reference).

In particular, according to the Merrifield technique, as it is commonly practiced, the C-terminal amino acid can be anchored to the support through formation of a benzyl ester with hydroxymethylphenylacetamidomethyl polystyrene (RAM resin). The Boc group can be used for temporary protection of the [alpha]-amino group. Removal of this group can be effected with neat trifluoroacetic acid (TFA) or TFA in dichloromethane (DCM). The resulting trifluoroacetate can be neutralized prior to coupling with e.g. diisopropylethylamine (DIPEA) in DCM or neutralized in situ during the coupling reaction. Coupling can be carried out by activation of the incoming amino acid with dicyclohexylcarbodiimide (DCC) in DCM or the use of pre-formed amino acid symmetrical anhydrides or benzotriazolyl esters in DMF or N-methylpyrrolidone (NMP). Release of the peptide from the resin and removal of the side chain protection groups can be effected with anhydrous hydrogen fluoride (HF).

Unlike the Merrifield approach which utilizes a regime of graduated acidolysis to achieve selectivity in the removal of protection, the Fmoc/tBu method is based on an orthogonal protection group strategy, using the base-labile Fmoc group for protection of the [alpha]-amino group and acid-labile side-chain protection groups. Since removal of protection can be effected by completely different chemical mechanisms, side-chain protection groups and linkage agents can be employed that are removed under considerably milder conditions than those used in the Merrifield approach. For instance, t-butyl- and trityl-based side-chain protection and alkoxybenzyl-based linkers can be used as they can be removed with TFA. The temporary Fmoc protection group can be removed with 20% piperidine in DMF. Coupling can be carried out in DMF or NMP with pre-formed active esters or using activation reagents that generate in situ benzotriazolyl esters. Cleavage of the peptide from the resin and global side-chain deprotection can be achieved with 95% TFA.

In one embodiment of the present invention, the first protection group is Fmoc. In another embodiment, the second protection group is an acid-labile protection group, optionally selected from the group consisting of t-Butoxycarbonyl (Boc) and Benzyloxycarbonyl (Z). In the context of the present invention, the term "acid-labile protection group" typically denotes protection groups that are stable under basic conditions, such as Boc and benzyl groups.

As noted above, any reactive "side groups" of the constituent amino acids are usually protected from unwanted chemical reactions throughout the chain assembly. In one embodiment, the histidine residue of the second peptide fragment is protected at the side chain with a protection group selected from the group consisting of Trityl (Trt), t-Butoxycarbonyl (Boc), Benzyloxymethyl (Bom) and t-Butoxymethyl (Bum). Further, the aspartic acid acid residue of the second peptide fragment can be protected at the side chain with a tert-butyl ester protection group.

In another embodiment of the present invention, prior to coupling the second peptide fragment to the N-terminally deprotected, support-conjugated first peptide fragment the second peptide fragment is cleaved from the support. Cleavage of protected fragments from the support is well-known to a person skilled in the art (e.g., see pages 216-220 in "Fmoc-Solid Phase Peptide Synthesis-A practical approach", W. C. Chan, P. D. White, Oxford University Press Inc. New York, 2000; being incorporated herein by reference).

In a specific embodiment, prior to coupling the second peptide fragment to the N-terminally deprotected, support-conjugated first peptide fragment the cleaved second peptide fragment is purified, optionally by chromatography and/or crystallization.

When used herein the term "purification" includes any separation method known in the art suitable for separating peptides from impurities such as chromatographic separation (such as affinity chromatography, ion exchange chromatography, hydrophobic interaction chromatography or reversed phase HPLC (High Pressure Liquid Chromatography)), Ultra Filtration (UF), iso-electric precipitation or any other suitable separation method.

In the context of the present invention, the term "chromatography" includes a set of laboratory techniques for the separation of mixtures. It usually involves passing a mixture dissolved in a "mobile phase" along a "stationary phase", which separates the peptides of interest from by-products in the mixture based on differential partitioning between the mobile and stationary phases. In the context of the present invention, liquid chromatography may be preparative or analytical. The purpose of preparative chromatography is usually to separate the components of a mixture for further use (and is thus a form of purification). Analytical chromatography is done normally with smaller amounts of material and is for measuring the relative proportions of analytes in a mixture. The two techniques are not mutually exclusive.

When used herein the term "crystallization" includes the separation of a peptide product from a liquid phase or feedstream, e.g. in extremely pure form, by cooling the liquid phase or feedstream or adding precipitants which lower the solubility of the desired product so that it forms crystals.

In a specific embodiment, prior to coupling the second peptide fragment to the N-terminally deprotected, support-conjugated first peptide fragment the cleaved second peptide fragment is purified by reversed phase HPLC.

According to another embodiment, the Fmoc protection group is removed from the first peptide fragment by adding a secondary amine selected from the group consisting of piperidine, piperazine, morpholine and dicyclohexylamine.

According to another embodiment, the inventive method further comprises cleaving the first peptide fragment coupled to the second peptide fragment from the support. In particular, the method according to the present invention may further comprise purifying the cleaved first peptide fragment coupled to the second peptide fragment, optionally by chromatography, e.g. by reversed-phase HPLC.

In a specific embodiment, the present invention thus relates to a method of preparing a peptide comprising the amino acid sequence His-Gly-Asp-Gly-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp (SEQ ID NO:1), the method comprising the steps of:

(a) providing, e.g. by solid phase peptide synthesis, a first peptide fragment comprising the amino acid sequence X-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp (SEQ ID NO:2) by peptide synthesis, wherein X is a Fmoc protection group and wherein the C-terminal residue of the first peptide fragment is conjugated to a support;

(b) providing, e.g. by solid phase peptide synthesis, a second peptide fragment comprising the amino acid sequence Y-His-Gly-Asp-Gly (SEQ ID NO:3) by peptide synthesis, wherein Y is an acid-labile protection group, optionally selected from the group consisting of Boc and benzyloxycarbonyl, and wherein the C-terminal residue of the second peptide fragment is conjugated to a support;

(c) cleaving the second peptide fragment from the support;

(d) optionally purifying the cleaved second peptide fragment, e.g. by chormatography such as reversed-phase high-pressure liquid chromatography and/or by crystallization;

(e) removing the Fmoc protection group from the first peptide fragment, optionally by adding a secondary amine selected from the group consisting of piperidine, piperazine, morpholine and dicyclohexylamine;

(f) coupling the second peptide fragment to the support-conjugated first peptide fragment by adding the purified second peptide fragment to the N-terminally deprotected, support-conjugated first peptide fragment;

(g) cleaving the support-conjugated first peptide fragment coupled to the second peptide fragment from the support; and (h) optionally purifying the cleaved first peptide fragment coupled to the second peptide fragment, e.g. by chormatography such as reversed-phase high-pressure liquid chromatography and/or by crystallization.

In principle every support which is known to be useful for solid phase peptide synthesis can be used for the method according to the present invention, see e.g. those described in Fmoc-Solid Phase Peptide Synthesis-A practical approach, W. C. Chan, P. D. White, Oxford University Press Inc. New York, 2000.

According to one embodiment, the support is a functionalized polymer or resin, optionally selected from the group consisting of polystyrene, polydimethylacrylamide and polyethylenglycol. Two practical procedures are commonly used, known as batchwise and continuous-flow, which differ principally in the method employed for washing of the resin between synthetic steps. In the batchwise process, the peptidyl resin is contained within a fritted reaction vessel, and reagents are added portionwise through the top of the vessel and removed by the appropriate application of positive nitrogen pressure or vacuum. In continuous-flow synthesis, the resin is packed into a column and washing is achieved by pumping solvent through the resin bed. Optionally, the method according to the present invention is a batchwise process.

The C-terminal amino acid of the first peptide fragment and/or the second peptide fragment can be attached to the functionalized polymer by means of a linker, which may be, optionally, 4-hydroxymethylphenoxyacetic acid (HMPA). However, in principle every linker which is known to be useful for solid phase peptide synthesis can be used for the methods of the invention. Suitable linkers are readily available and well-known to a person skilled in the art (e.g., see pages 15-19 in "Fmoc-Solid Phase Peptide Synthesis-A practical approach", W. C. Chan, P. D. White, Oxford University Press Inc. New York, 2000; being incorporated herein by reference).

In some embodiments, the first peptide fragment and/or the second peptide fragment can be cleaved from the support by means of an acid, optionally selected from the group consisting of trifluoroacetic acid (TFA), trifluoromethanesulfonic acid (TFMSA), hydrogen bromide (HBr), hydrogen chloride (HCl) and hydrogen fluoride (HF), or by means of a base, optionally a hydroxide.

In a further aspect, the present invention relates to a method of preparing a pharmaceutical composition containing a peptide comprising the amino acid sequence His-Gly-Asp-Gly-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp (SEQ ID NO:1), the method comprising the steps of:

(a) preparing the peptide according to the method of the present invention as described above; and (b) preparing a pharmaceutical composition containing the peptide prepared in step (a).

Hence, the present invention further provides commercially suitable pharmaceutical compositions of a peptide comprising the amino acid sequence of SEQ ID NO:1, which compositions can be prepared using a commercially acceptable process. As used herein, "preparation", "formulation" and "composition" may be used interchangeably herein, and refer to a combination of two or more elements, or substances.

As used herein, "pharmaceutical composition" may be used to refer to a composition that has measurable specified or selected physiologic activity when administered to a subject in a significant or effective amount. The composition according to the present invention incorporates teduglutide in a medically effective amount, namely an amount which is useful either therapeutically or diagnostically. Such an amount can be determined on the intended end-use of the composition. Therapeutically useful amounts of teduglutide are commonly known to a person skilled in the art.

As used herein, "effective amount", and "sufficient amount" may be used interchangeably and refer to an amount of teduglutide which, when included in a composition, is sufficient to achieve an intended compositional or physiological effect. Thus, a "therapeutically effective amount" refers to a non-toxic, but sufficient amount of the pharmaceutically active peptide, to achieve therapeutic, preservative or diagnostic results in treating a condition for which the pharmaceutically active peptide is known to be effective.

It is understood that various biological factors may affect the ability of a substance to perform its intended function. Therefore, an "effective amount" or a "therapeutically effective amount" may be dependent in some instances on such biological factors.

Further, while the achievement of therapeutic effects may be measured by a physician or other qualified medical personnel using evaluations known in the art, it is recognized that individual variation and response to treatments may make the achievement of therapeutic effects a subjective decision. The determination of an effective amount is well within the ordinary skill in the art of pharmaceutical sciences and medicine.

In one embodiment, the pharmaceutical composition further comprises phosphate buffer in an amount sufficient to adjust the pH of the composition to a physiologically tolerable level. The term "buffer" as used herein refers to a chemical compound that reduces the tendency of pH of a solution such as chromatographic solutions to change over time as would otherwise occur. Suitable buffers include, but are not limited to acetate, carbonate, citrate, glycylglycine, glycine, histidine, lysine, phosphate, borate, Trishydroxymethyl-aminomethane, ethanolamine and mixtures thereof. Usually, the pH of the composition is greater than about 5.5, e.g. greater than about 6, such as from about 6.9 to about 7.9, or from about 7.3 to about 7.4. In particular, the buffering agent can be phosphate based, and in some embodiments a 35 mM phosphate buffer is used.

In another embodiment, the pharmaceutical composition further comprises a bulking agent selected from the group consisting of mannitol and sucrose. The bulking agent incorporated in the composition may produce a non-crystalline amorphous cake.

According to still another embodiment, the pharmaceutical composition further comprises pharmaceutically acceptable excipients. For instance, the composition can additionally comprise an isotonic agent (i.e. an isotonicity modifier), e.g. a physiologically tolerated inorganic salt, such as sodium chloride or potassium chloride, or a physiologically tolerated sugar or sugar alcohol for example, sorbitol, or a physiologically tolerated amino acid. In particular, the pharmaceutical composition may further comprise L-histidine.

According to another embodiment, the pharmaceutical composition is provided as an injectable dosage form. According to another embodiment, the pharmaceutical composition is provided as a parenteral dosage form. In one application, the composition according to the present invention may be exploited for the treatment of gastrointestinal disease, particularly diseases, disorders or conditions of the intestine.

As used herein, "administration", and "administering" refer to the manner in which teduglutide, or composition containing such, is presented to a subject. As used herein, "subject" refers to a mammal that may benefit from the administration of a composition or method as recited herein. Most often, the subject will be a human but can be other animals.

According to a specific embodiment of the present invention, the composition comprises:
(a) a medically useful amount of teduglutide prepared according to the method of the present invention as described above;
(b) a phosphate buffer sufficient to adjust the pH of the formulation to a pharmaceutically acceptable level, and in particular between from about 6.0 to about 9.0 such as between from about 6.5 to about 8.0 or between from about 7.0 to about 7.5;
(c) a stabilizing amount of the amino acid L-histidine; and
(d) a bulking agent selected from sucrose and mannitol.

In particular, the composition may comprise:
(a) a medically useful amount of teduglutide prepared according to the method of the present invention as described above comprising from about 0.1 to about 50 mg/ml of the peptide, e.g. about 5 to about 40 mg/ml, or about 7 to about 30 mg/ml, or about 10 to about 20 mg/ml, or about 20 mg/ml;
(b) a phosphate buffer to maintain the pH at a physiologically tolerable level, e.g., above 5.5 or 6 and in particular between from about 6.0 to about 9.0 such as between from about 6.5 to about 8.0 or between from about 7.0 to about 7.5;
(c) a stabilizing amino acid, particularly L-histidine; and
(d) a bulking agent, particularly mannitol.

In particular, the composition may be a lyophilized formulation comprising in the reconstituted product:
(a) phosphate buffer in an amount necessary to maintain the pH of the reconstituted product from about 6.9-7.9, or e.g. in an amount to maintain a pH of about 7.3 to about 7.4;
(b) about 0.5 to about 1% L-histidine;
(c) about 2 to about 5% mannitol, e.g. about 2.5 to about 3.5% mannitol, or about 3% mannitol; and
(d) from about 0.1 to about 50 mg/ml of teduglutide prepared according to the method of the present invention as described above, e.g. about 5 to about 40 mg/ml, or about 7 to about 30 mg/ml, or about 10 to about 20 mg/ml, or about 20 mg/ml.

In a specific embodiment of the invention, the composition may be a lyophilized composition comprising in the reconstituted product:
(a) about 7 to about 30 mg/ml, e.g. about 10 to about 20 mg/ml, or about 20 mg/ml of teduglutide prepared according to the method of the present invention as described above;
(b) a phosphate buffer sufficient to maintain the pH at about 7.3 to about 7.4;
(c) about 0.5 to about 1% L-histidine; and
(d) about 3% mannitol.

In the context of the present invention, freeze-drying (also known as lyophilization or cryodesiccation) includes a dehydration process typically used to preserve a peptide or make a peptide more convenient for transport. Freeze-drying usually works by freezing the liquid composition comprising the peptide and then reducing the surrounding pressure and adding enough heat to allow the frozen water in the composition to sublimate directly from the solid phase to the gas phase.

Accordingly, the present compositions can also be provided in lyophilized form, e.g., as freeze-dried powders suitable for reconstitution and subsequent administration as injectable liquid compositions. To reconstitute, the sterile water may be drawn into a syringe and then transferred to the vial containing the lyophilized composition. The lyophilized compositions of the present invention are usually provided in a powder form comprising not more than about 5% water by weight, e.g. not more than 2% water by weight, or even not more than about 1% water by weight.

In another aspect of the present invention a process for making the lyophilized composition of a peptide comprising the amino acid sequence of SEQ ID NO:1 is provided. Such a process comprises the following steps:
(a) preparing the peptide according to the inventive method;
(b) preparing the composition according to the inventive method;
(c) freezing the composition to about −40° C.;
(d) performing a first drying step at about −20° C.; and
(e) performing a second drying step at +20° C.

In another embodiment, the composition subjected to the lyophilization process comprises:
(a) teduglutide prepared according to the method of the present invention as described above;
(b) 35 mM phosphate buffer to maintain the reconstituted product at a pH of about 6.9 to about 7.9, e.g. at a pH of about 7.3 to about 7.4;
(c) about 0.5 to about 1% L-histidine; and
(d) about 3% mannitol.

In a further aspect, the present invention relates to a peptide comprising the amino acid sequence His-Gly-Asp-Gly-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr- Lys-Ile-Thr-Asp (SEQ ID NO:1), the peptide being obtainable by the method of the present invention as described above.

In some embodiments, the methods of the invention are performed in a high-throughput format. In a further embodiment, the invention relates to the use of a method, as described herein, for the preparation of a peptide comprising the amino acid sequence of SEQ ID NO:1.

While the above invention has been described with respect to some of its embodiments, this is in no way to limit the scope of the invention. The person skilled in the art is clearly aware of further embodiments and alterations to the previously described embodiments that are still within the scope of the present invention.

EXAMPLES

Example 1—Peptide-Polymer Support Assembly

```
                                                (SEQ ID NO: 1)
H-His-Gly-Asp-Gly-Ser-Phe-Ser-Asp-Glu-Met-Asn-Thr-

Ile-Leu-Asp-Asn-Leu-Ala-Ala-Arg-Asp-Phe-Ile-Asn-

Trp-Leu-Ile-Gln-Thr-Lys-Ile-Thr-Asp-OH
```

1. Fmoc-Asp(OBu$^t$)—OH (1.235 g, 3 mmol) (Fmoc=9-fluorenylmethyloxycarbonyl) and Diisopropylcarbodiimide (0.623 g, 4 mmol) (DIC) were added to 4-hydroxymethylphenoxyacetic acid-dimethylacrylamide polymer support (1 g, 1 mmol) in N,N-dimethylformamide (15 cm$^3$) (DMF) followed by 4-dimethylamino pyridine (0.012 g, 0.1 mmol) (DMAP). This esterification was allowed to proceed for 1 h. The polymer support was washed with DMF (10×10 cm$^3$) and the reaction repeated. The polymer support was again washed with DMF (10×10 cm$^3$).
2. Piperidine/DMF (20 cm$^3$, 20% v/v) was added to the solid support. The reaction was allowed to stand for 3 minutes. A second treatment with Piperidine/DMF (20 cm$^3$, 20% v/v) for 7 minutes was carried out and the polymer support washed with DMF (10×10 cm$^3$).
3. Fmoc-Thr(Bu$^t$)—OH (0.994 g, 2.5 mmol) and 2-(1H-benzotriazol-1-yl)-N, N,N',N'-tetramethyluronium tetrafluoroborate (TBTU) (0.755 g, 2.35 mmol) were dissolved in DMF (10 cm$^3$). 4-Methylmorpholine (NMM) (0.33 cm$^3$, 3 mmol) was added and the mixture pre-activated for 2-3 minutes before adding to the polymer support. The coupling reaction was monitored to completion by Ninhydrin assay. The polymer support was then washed with DMF (10×10 cm$^3$).
4. Piperidine/DMF (20 cm$^3$, 20% v/v) was added to the solid support. The reaction was allowed to stand for 3 minutes. A second treatment with Piperidine/DMF (20 cm$^3$, 20% v/v) for 7 minutes was carried out and the polymer support washed with DMF (10×10 cm$^3$)

Fmoc-Ile-OH (0.884 g, 2.5 mmol) was then coupled and treated with piperidine/DMF using the procedure set out in 3-4 above with the exception that Fmoc-Ile-OH was used instead of Fmoc-Thr(Bu$^t$)—OH.

The assembly of the full peptide sequence was assembled in a stepwise fashion as described in steps 3-4 above. Repeated couplings were carried out as necessary to achieve a negative Ninhydrin assay. Peptides were synthesized batchwise in a suitable vessel and suitable common protection groups for side-chain functionalities. All reagents used are commercially available.

Following Fmoc removal at position 5, half of the polymer support was removed for extended piperidine treatment and one quarter was removed for fragment coupling.

Assembly was continued on half of the polymer support as described above but the peptide-polymer support was treated for an additional 20 minutes with piperidine in DMF during Fmoc removal to mimic the extended reaction time that might be observed when performing the synthesis at industrial scale.

Assembly was continued on one quarter of the peptide-polymer support using the standard protocols described above.

The protected tetrapeptide fragment Boc-His(Trt)-Gly-Asp(OBu$^t$)-Gly-OH was prepared on H-Gly-2-chlorotrityl-polystyene polymer support at 1 mmol scale using the standard protocols analogous to those described above.

Example 2—Teduglutide Cleavage

The two completely assembled teduglutide-polymer support samples were each washed thoroughly with dichloromethane and trifluoroacetic acid (TFA) containing triisopropylsilane (5% v/v) (TIPS) was added to affect the cleavage.

TFA and TIPS were removed by evaporation and the peptide triturated with diethyl ether to remove any remaining TIPS.

Example 3—Cleavage of Boc-His(Trt)-Gly-Asp(OBu$^t$)-Gly-OH

The protected tetrapeptide was cleaved from the chlorotrityl-polystyrene polymer support using TFA in dichloromethane (1% v/v, 6×10 cm$^3$). Each portion of TFA/dichloromethane was drawn into pyridine in methanol (2% v/v, 40 cm$^3$) to neutralise the acid.

The solvent was removed by rotary evaporation prior to purification.

Example 4—Purification of Boc-His(Trt)-Gly-Asp(OBu$^t$)-Gly-OH

The Boc-His(Trt)-Gly-Asp(OBu$^t$)-Gly-OH was purified on a Luna C18 reversed phase column (15 μm, 5 cm diameter×25 cm) using the following conditions.
Buffer A=water
Buffer B=MeCN
Gradient: 20-40% B over 60 minutes followed by 40-90% B over 60 minutes
Wavelength: 230 nm Example 5—Fragment Coupling The purified Boc-His(Trt)-Gly-Asp(OBu$^t$)-Gly-OH was coupled to peptide-polymer support truncated at position 5 at 55 μmol scale applying the standard coupling procedure using TBTU described above for Fmoc-amino acid couplings.

The peptide was cleaved from the polymer support as described in Example 2 on a reduced scale.

Example 6—Analysis of Crude Peptides

The three batches of crude peptide were analysed by reversed phase HPLC on a Vydac C18 column (5 μm, 4.6 mm×250 mm) using the following conditions.

Buffer A=0.1% v/v TFA/water
Buffer B=0.1% v/v TFA/MeCN
Gradient: 1-99% B over 20 minutes
Wavelength: 230 nm Example 7—HPLC Results The full teduglutide molecule was assembled using the Fmoc-solid phase protocols described above. The purity of the crude peptide assembled was 52% by HPLC and contained 24% of the [beta]-Asp analogue (see FIG. 1).

The full teduglutide molecule was also assembled using extended piperidine treatment for the last 4 amino acids in order to demonstrate the effect of increasing the contact time with base that could be observed at large scale. This crude peptide was 39% pure and contained 45% [beta]-Asp analogue (see FIG. 2).

Furthermore, the 5-33 fragment was assembled on the solid phase using the Fmoc-solid phase protocols described above. The protected tetrapeptide Boc-His(Trt)-Gly-Asp (OBut)-Gly-OH was assembled and purified prior to coupling to the 5-33 fragment on the solid phase. The tetrapeptide was cleaved from the support, purified, and coupled to the 5-33 fragment which was still coupled to its solid support. The crude peptide from this assembly was 59% pure and contained 17% of the [beta]-Asp analogue (see FIG. 3).

In summary, the ratio of linear to branched molecule in the standard assembly was 2.18. The ratio in the assembly with extended piperidine treatment was 0.88. The ratio of the linear peptide to the branched [beta]-Asp analogue in the two fragment assembly was 3.52. Hence, this data clearly demonstrates a significant reduction of the level of the [beta]-Asp analogue in the two fragment assembly according to the present invention as described above.

Without wishing to be bound by any theory, it is believed that a crude purity of 80% or more is achievable, as only a simple tetrapeptide purification step was carried out in the examples reported above and further optimization of the steps described above is well known to the person skilled in the art. This would potentially significantly reduce the cost and scale of manufacture with a concurrent reduction of the burden on the purification stage.

Some embodiments of the invention relate to:
1. A method of preparing a peptide comprising the amino acid sequence His-Gly-Asp-Gly-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp (SEQ ID NO:1), the method comprising the steps of:
(a) providing a first peptide fragment comprising the amino acid sequence X-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp (SEQ ID NO:2), wherein X is a first protection group and the C-terminal residue of the first peptide fragment is conjugated to a support;
(b) providing a second peptide fragment comprising the amino acid sequence Y-His-Gly-Asp-Gly (SEQ ID NO:3), wherein Y is a second protection group;
(c) removing the first protection group from the first peptide fragment; and
(d) coupling the second peptide fragment to the N-terminal deprotected, support-conjugated first peptide fragment.
2. The method of 1, wherein the first peptide fragment and/or the second peptide fragment are prepared by solid phase peptide synthesis.
3. The method of 2, wherein the first peptide fragment and/or the second peptide fragment are provided by conjugating the C-terminal amino acid residue to a support and sequentially adding appropriately protected amino acids to the N-terminus of the C-terminal, support-conjugated residue(s).
4. The method of 3, wherein amino acids to be sequentially added to the N-terminus of the C-terminal, support-conjugated residue(s) of the first peptide fragment and/or the second peptide fragment are each protected by a protection group selected from the group consisting of Boc and Fmoc.
5. The method of any of 1 to 4, wherein the first protection group is Fmoc.
6. The method of any of 1 to 5, wherein the second protection group is an acid-labile protection group, optionally selected from the group consisting of Boc and benzyloxycarbonyl.
7. The method of any of 1 to 6, wherein the histidine residue of the second peptide fragment is protected at the side chain with a protection group selected from the group consisting of trityl, Boc, Bom and Bum.
8. The method of any of 1 to 7, wherein the aspartic acid acid residue of the second peptide fragment is protected at the side chain with a tert-butyl ester protection group.
9. The method of any of 3 to 8, wherein prior to coupling the second peptide fragment to the N-terminal deprotected, support-conjugated first peptide fragment the second peptide fragment is cleaved from the support.
10. The method of 9, wherein prior to coupling the second peptide fragment to the N-terminal deprotected, support-conjugated first peptide fragment the cleaved second peptide fragment is purified, optionally by chromatography and/or crystallization.
11. The method of any of 5 to 10, wherein the Fmoc protection group is removed from the first peptide fragment by adding a secondary amine selected from the group consisting of piperidine, piperazine, morpholine and dicyclohexylamine.
12. The method of any of 1 to 11, further comprising cleaving the first peptide fragment coupled to the second peptide fragment from the support.
13. The method of 12, further comprising purifying the cleaved first peptide fragment coupled to the second peptide fragment, optionally by chromatography.
14. The method of any of 1 to 13, comprising:
(a) providing a first peptide fragment comprising the amino acid sequence X-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp (SEQ ID NO:2) by peptide synthesis, wherein X is a Fmoc protection group and the C-terminal residue of the first peptide fragment is conjugated to a support;
(b) providing a second peptide fragment comprising the amino acid sequence Y-His-Gly-Asp-Gly (SEQ ID NO:3) by peptide synthesis, wherein Y is an acid-labile protection group, optionally selected from the group consisting of Boc and benzyloxycarbonyl, and the C-terminal residue of the second peptide fragment is conjugated to a support;
(c) cleaving the second peptide fragment from the support;
(d) purifying the cleaved second peptide fragment, optionally by reversed-phase high-pressure liquid chromatography;
(e) removing the Fmoc protection group from the first peptide fragment, optionally by adding a secondary amine selected from the group consisting of piperidine, piperazine, morpholine and dicyclohexylamine;
(f) coupling the second peptide fragment to the support-conjugated first peptide fragment by adding the purified second peptide fragment to the N-terminal deprotected, support-conjugated first peptide fragment;

(g) cleaving the support-conjugated first peptide fragment coupled to the second peptide fragment from the support; and
(h) purifying the cleaved first peptide fragment coupled to the second peptide fragment, optionally by reversed-phase high-pressure liquid chromatography.

15. The method of any of 1 to 14, wherein the support is a functionalized polymer, optionally selected from the group consisting of polystyrene, polydimethylacrylamide and polyethylenglycol.

16. The method of 15, wherein the C-terminal amino acid of the first peptide fragment and/or the second peptide fragment is attached to the functionalized polymer by means of a linker, optionally 4-hydroxymethylphenoxyacetic acid (HMPA).

17. The method of any of 1 to 16, wherein the first peptide fragment and/or the second peptide fragment are cleaved from the support by means of an acid, optionally selected from the group consisting of trifluoroacetic acid (TFA), trifluoromethanesulfonic acid (TFMSA), hydrogen bromide (HBr), hydrogen chloride (HCl) and hydrogen fluoride (HF), or by means of a base, optionally a hydroxide.

18. A method of preparing a pharmaceutical composition containing a peptide comprising the amino acid sequence His-Gly-Asp-Gly-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp (SEQ ID NO:1), the method comprising the steps of:
(a) preparing the peptide according to the method of any of 1 to 17; and
(b) preparing a pharmaceutical composition containing the peptide prepared in step (a).

19. The method of 18, wherein the pharmaceutical composition further comprises phosphate buffer in an amount sufficient to adjust the pH of the composition to a physiologically tolerable level.

20. The method of 18 or 19, wherein the pharmaceutical composition further comprises L-histidine.

21. The method of any of 18 to 20, wherein the pharmaceutical composition further comprises a bulking agent selected from the group consisting of mannitol and sucrose.

22. The method of any of 18 to 21, wherein the pharmaceutical composition is provided as an injectable dosage form.

The invention claimed is:

1. A method of preparing a peptide comprising the amino acid sequence His-Gly-Asp-Gly-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp (SEQ ID NO:1) via a fragment-based assembly, the method comprising the steps of:
   (a) providing a first peptide fragment comprising the amino acid sequence X-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp (SEQ ID NO:2), wherein X is a first protection group and wherein the C-terminal residue of the first peptide fragment is conjugated to a support;
   (b) providing a second peptide fragment comprising the amino acid sequence Y-His-Gly-Asp-Gly (SEQ ID NO:3), wherein Y is a second protection group;
   (c) removing the first protection group from the first peptide fragment; and
   (d) coupling the second peptide fragment to the N-terminally deprotected, support-conjugated first peptide fragment;
   wherein aspartamide by-product formation is reduced during preparation of the peptide via the fragment-based assembly in comparison to a peptide comprising the amino acid sequence of SEQ ID NO:1 prepared by a non-fragment based assembly.

2. The method of claim 1, wherein the first peptide fragment and/or the second peptide fragment are prepared by solid phase peptide synthesis, and wherein optionally, in case the second peptide fragment is prepared by solid phase peptide synthesis, the second peptide fragment is cleaved from the support prior to coupling the second peptide fragment to the N-terminally deprotected first peptide fragment, and/or wherein optionally, in case the first peptide fragment is prepared by solid phase peptide synthesis, the first peptide fragment coupled to the second peptide fragment is cleaved from the support.

3. The method of claim 2, wherein the first peptide fragment and/or the second peptide fragment are provided by conjugating the C-terminal amino acid residue to a support and sequentially adding appropriately protected amino acids to the N-terminus of the C-terminal, support-conjugated residue(s).

4. The method of claim 3, wherein amino acids to be sequentially added to the N-terminus of the C-terminal, support-conjugated residue(s) of the first peptide fragment and/or the second peptide fragment are each protected by a protection group selected from the group consisting of Boc and Fmoc.

5. The method of claim 1, wherein the first protection group is Fmoc.

6. The method of claim 1, wherein the second protection group is an acid-labile protection group, selected from the group consisting of Boc and benzyloxycarbonyl.

7. The method of claim 1, wherein the histidine residue of the second peptide fragment is protected at the side chain with a protection group selected from the group consisting of trityl, Boc, Bom and Bum.

8. The method of claim 1, wherein the aspartic acid residue of the second peptide fragment is protected at the side chain with a tert-butyl ester protection group.

9. The method of claim 1, comprising:
   (a) providing by solid phase synthesis a first peptide fragment comprising the amino acid sequence X-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp (SEQ ID NO:2) by peptide synthesis, wherein X is a Fmoc protection group and wherein the C-terminal residue of the first peptide fragment is conjugated to a support;
   (b) providing by solid phase synthesis a second peptide fragment comprising the amino acid sequence Y-His-Gly-Asp-Gly (SEQ ID NO:3) by peptide synthesis, wherein Y is an acid-labile protection group, selected from the group consisting of Boc and benzyloxycarbonyl, and wherein the C-terminal residue of the second peptide fragment is conjugated to a support;
   (c) cleaving the second peptide fragment from the support;
   (d) optionally purifying the cleaved second peptide fragment;
   (e) removing the Fmoc protection group from the first peptide fragment, by adding a secondary amine selected from the group consisting of piperidine, piperazine, morpholine and dicyclohexylamine;
   (f) coupling the second peptide fragment to the support-conjugated first peptide fragment by adding the purified second peptide fragment to the N-terminally deprotected, support-conjugated first peptide fragment;
   (g) cleaving the support-conjugated first peptide fragment coupled to the second peptide fragment from the support; and
   (h) optionally purifying the cleaved first peptide fragment coupled to the second peptide fragment, wherein optionally the support is a functionalized polymer.

10. The method of claim 9, wherein the C-terminal amino acid of the first peptide fragment and/or the second peptide fragment is attached to the functionalized polymer by means of a linker.

11. A method of preparing a pharmaceutical composition containing a peptide comprising the amino acid sequence His-Gly-Asp-Gly-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp (SEQ ID NO:1), the method comprising the steps of:
   (a) preparing the peptide according to the method of claim 1; and
   (b) preparing a pharmaceutical composition containing the peptide prepared in step (a).

12. The method of claim 11, wherein the pharmaceutical composition further comprises phosphate buffer in an amount sufficient to adjust the pH of the composition to a physiologically tolerable level.

13. The method of claim 11, wherein the pharmaceutical composition further comprises L-histidine.

14. The method of claim 11, wherein the pharmaceutical composition further comprises a bulking agent selected from the group consisting of mannitol and sucrose.

15. The method of claim 11, wherein the pharmaceutical composition is provided as an injectable dosage form.

16. The method of claim 1, further comprising purifying the second peptide fragment to remove a [beta]-Asp analogue prior to coupling the second peptide fragment to the first peptide fragment.

* * * * *